(12) United States Patent
Noy

(10) Patent No.: US 7,127,099 B2
(45) Date of Patent: Oct. 24, 2006

(54) IMAGE SEARCHING DEFECT DETECTOR

(75) Inventor: Amir Noy, Kfar Mordehai (IL)

(73) Assignee: Orbotech Ltd., Yavne (IL)

( * ) Notice: Subject to any disclaimer, the term of this patent is extended or adjusted under 35 U.S.C. 154(b) by 618 days.

(21) Appl. No.: 10/142,065

(22) Filed: May 10, 2002

(65) Prior Publication Data

US 2002/0168099 A1 Nov. 14, 2002

Related U.S. Application Data

(60) Provisional application No. 60/290,010, filed on May 11, 2001.

(51) Int. Cl.
*G06K 9/00* (2006.01)

(52) U.S. Cl. .................. 382/149; 382/145; 356/237.1

(58) Field of Classification Search ............. 382/144, 382/141, 145, 212, 149; 257/E21.23; 250/550; 430/30; 356/399, 237.5, 237.1
See application file for complete search history.

(56) References Cited

U.S. PATENT DOCUMENTS

| | | | | |
|---|---|---|---|---|
| 4,928,313 | A * | 5/1990 | Leonard et al. | 382/149 |
| 5,023,916 | A * | 6/1991 | Breu | 382/150 |
| 6,148,099 | A * | 11/2000 | Lee et al. | 382/149 |
| 6,175,417 | B1 | 1/2001 | Do et al. | |
| 6,185,511 | B1 | 2/2001 | Steffan et al. | |
| 6,222,935 | B1 | 4/2001 | Okamoto | |
| 6,363,167 | B1 * | 3/2002 | Miyano et al. | 382/145 |
| 6,452,677 | B1 * | 9/2002 | Do et al. | 356/394 |
| 6,614,924 | B1 * | 9/2003 | Aghajan | 382/149 |
| 6,757,421 | B1 * | 6/2004 | Kubo | 382/149 |
| 6,771,806 | B1 * | 8/2004 | Satya et al. | 382/149 |

FOREIGN PATENT DOCUMENTS

| | | |
|---|---|---|
| WO | WO 98/14892 | 4/1998 |
| WO | WO 99/01842 | 1/1999 |
| WO | WO 99/67626 | 12/1999 |
| WO | WO 00/03234 | 1/2000 |
| WO | WO 00/28473 | 5/2000 |
| WO | WO 00/73994 | 12/2000 |
| WO | WO 00/79472 | 12/2000 |

OTHER PUBLICATIONS

Haruo Yoda et al., "An Automatic Wafer Inspection System Using Pipelined Image Processing Techniques", IEEE Transaction on pattern analysis and machine intelligence, vol. 10, No. 1, Jan. 1988,pp. 4-16.*

Haruo Yoda"an automatic wafer inspection system using pipelined image processing techniques". IEEE transcation on pattern analysis and machine intelligence. vol. 10, No. 1, Jan. 1988.*

(Continued)

*Primary Examiner*—Sheela Chawan
(74) *Attorney, Agent, or Firm*—Sughrue Mion, PLLC

(57) ABSTRACT

An image of an article to be inspected is divided into image portions, and a search engine makes a comparison with the image portion and a library of reference images. The reference images have predetermined labels that indicate whether each indicates a defect or no defect. The one of the reference images that most closely matches the image portion is determined, and the label associated with the reference image is taken as indicating whether the image portion corresponds to a location with a defect or no defect. Locations indicated as being defective are considered candidate defects and may subsequently be inspected in more detail.

27 Claims, 6 Drawing Sheets

OTHER PUBLICATIONS

Brochure: *SK-75™ AOI Inspection System, Advanced Inspection for Process Sampling and Volume Production*, Orbotech Ltd.

Product Information on SK-75™ AOI Inspection System, Orbotech Ltd., Orbotech Website: http:www.Orbotech.com/products_mi_sk75.html.

Brochure: *INSPIRE-9060™ Specifications*, Orbotech Ltd.

Product Information on INSPIRE-9000™ Automated Optical Inspection System, Orbotech Ltd., Orbotech Website: http:www.Orbotech.com/products_mi_inspire9000.html.

Shimon Cohen et al.,*Automatic model selection in a hybrid perception/radical network*, Computer Science Dept., Tel-Aviv University, Nov. 15, 2001, pp. 1-23.

Shimon Cohen et al., *Forward and backward selection in regression hybrid network*, Computer Science Dept., Tel-Aviv University, pp. 1-10.

Chou et al., *Automatic defect classification for semiconductor manufacturing*, Machine Vision and Applications 9: 201-214 (1997).

Brzakovic et al., *Designing a defect classification system: a case study*, Pattern Recognition, vol. 29, No. 8, pp. 1401-1419, 1996.

Choon-Woo Kim et al., *Hierarchical classification of surface defects on dusty wood boards*, Pattern Recognition Letters 15, pp. 713-721, Jul. 1994.

Hennessey et al., *Integrated Defect Management Using a Knowledge-Based Approach*, Semiconductor International, vol. 19, No. 11 (1996) pp. 177-184.

Breaux et al., *Automatic defect classification for effective yield management*, Solid State Technology, Dec. 1996, pp. 89-96.

Chen-Ting Lin et al., *Defect Reduction in a High-Volume Fab*, Semiconductor International, Jul. 2001, pp. 159-166.

Byron et al., *Recent advances in the automatic inspection of integrated circuits for pattern defects*, Machine Vision and Applications 8: pp. 5-19, 1995.

Petra Perner, *A knowledge-based image-inspection system for automatic defect recognition, classification, and process diagnosis*, Machine Vision and Applications 7: pp. 135-147, 1994.

Operation Manual: *Defect Classification Station*, KLA-Acrotec, Version 1.0 & 2.0, Jul. 1, 1998.

S. Cohen and N. Intrator, *A hybrid projection based and radial basis function architecture*, School of Computer Science, Tel-Aviv University, Israel, pp. 1-15, Oct. 2001.

* cited by examiner

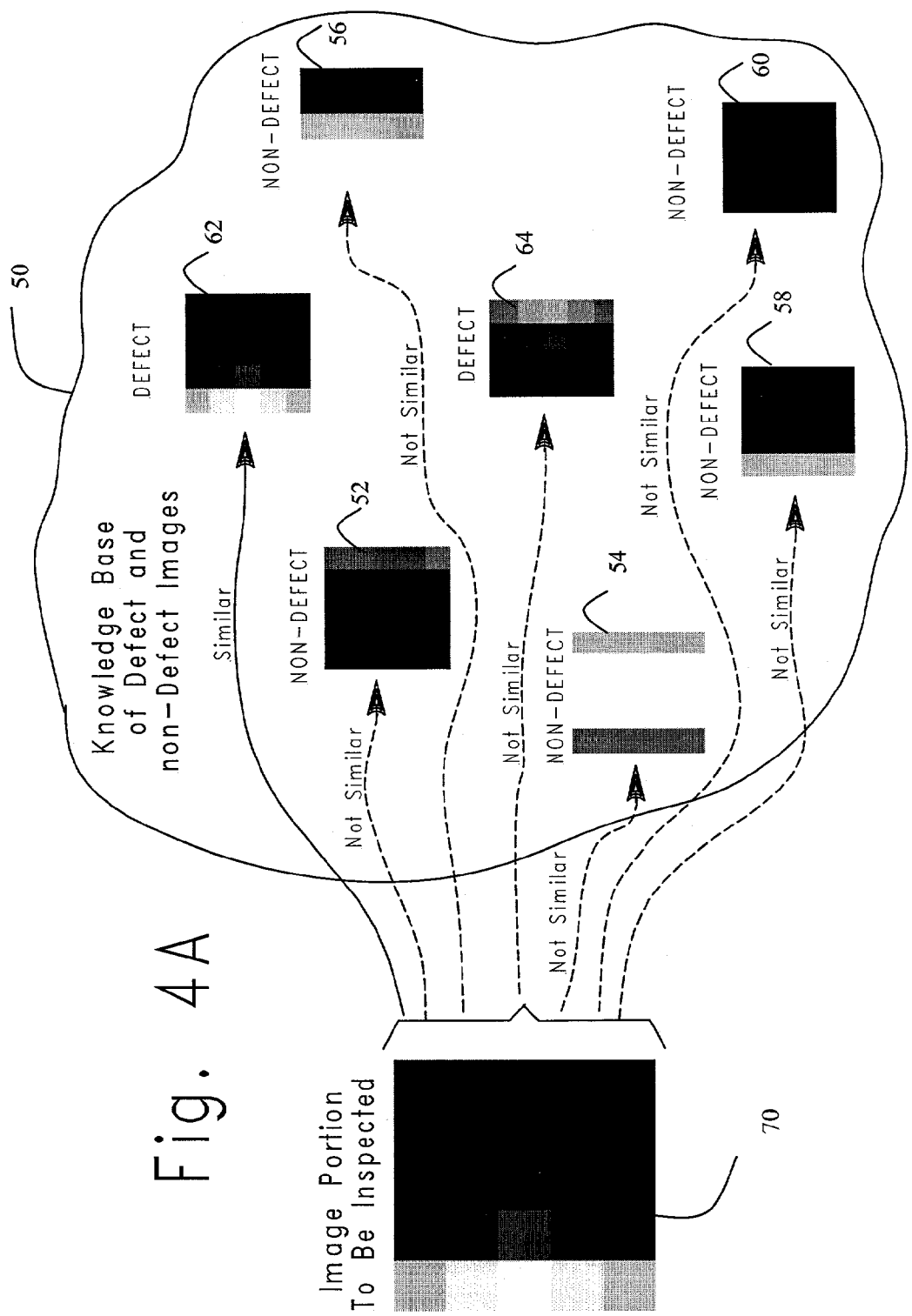

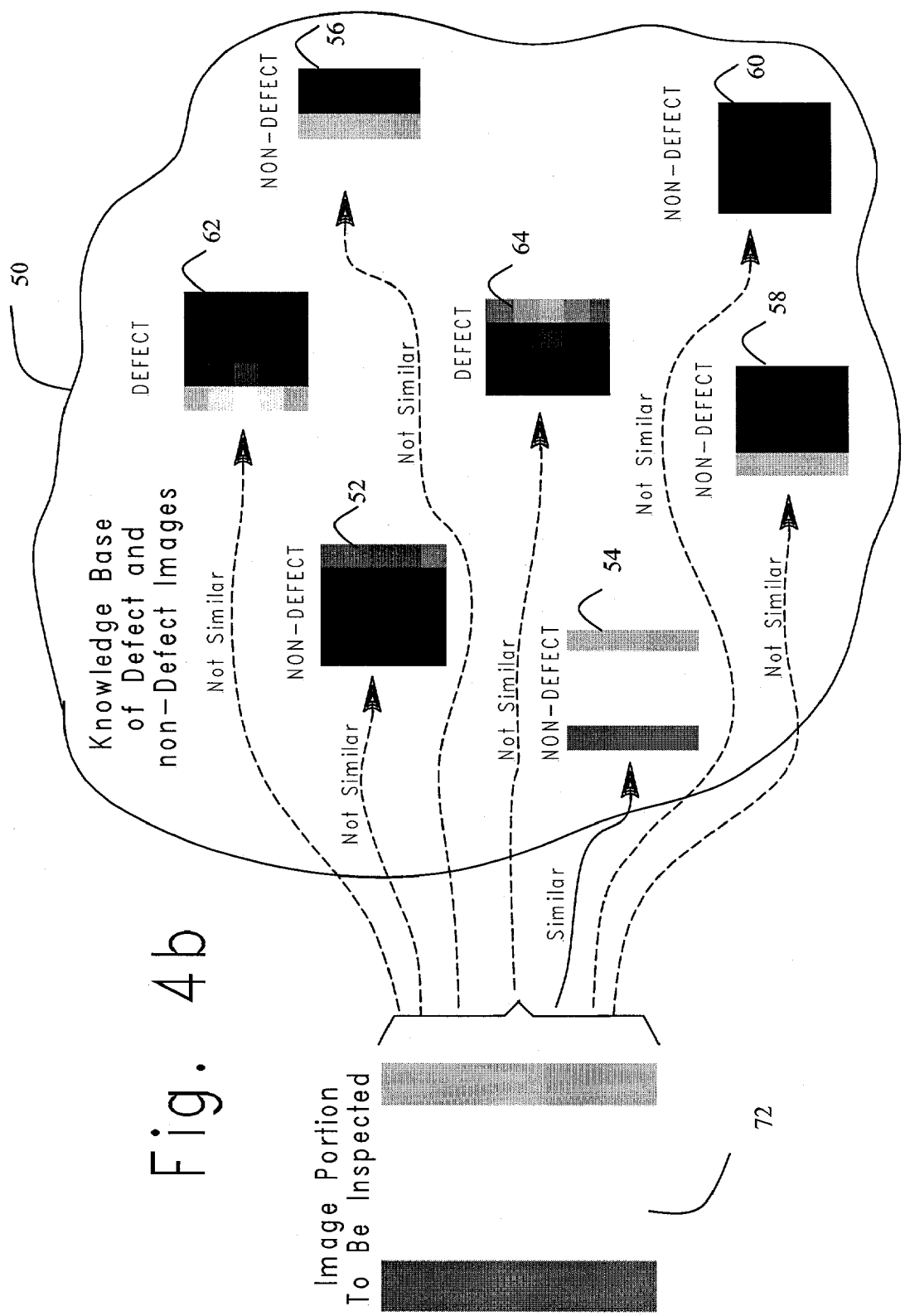

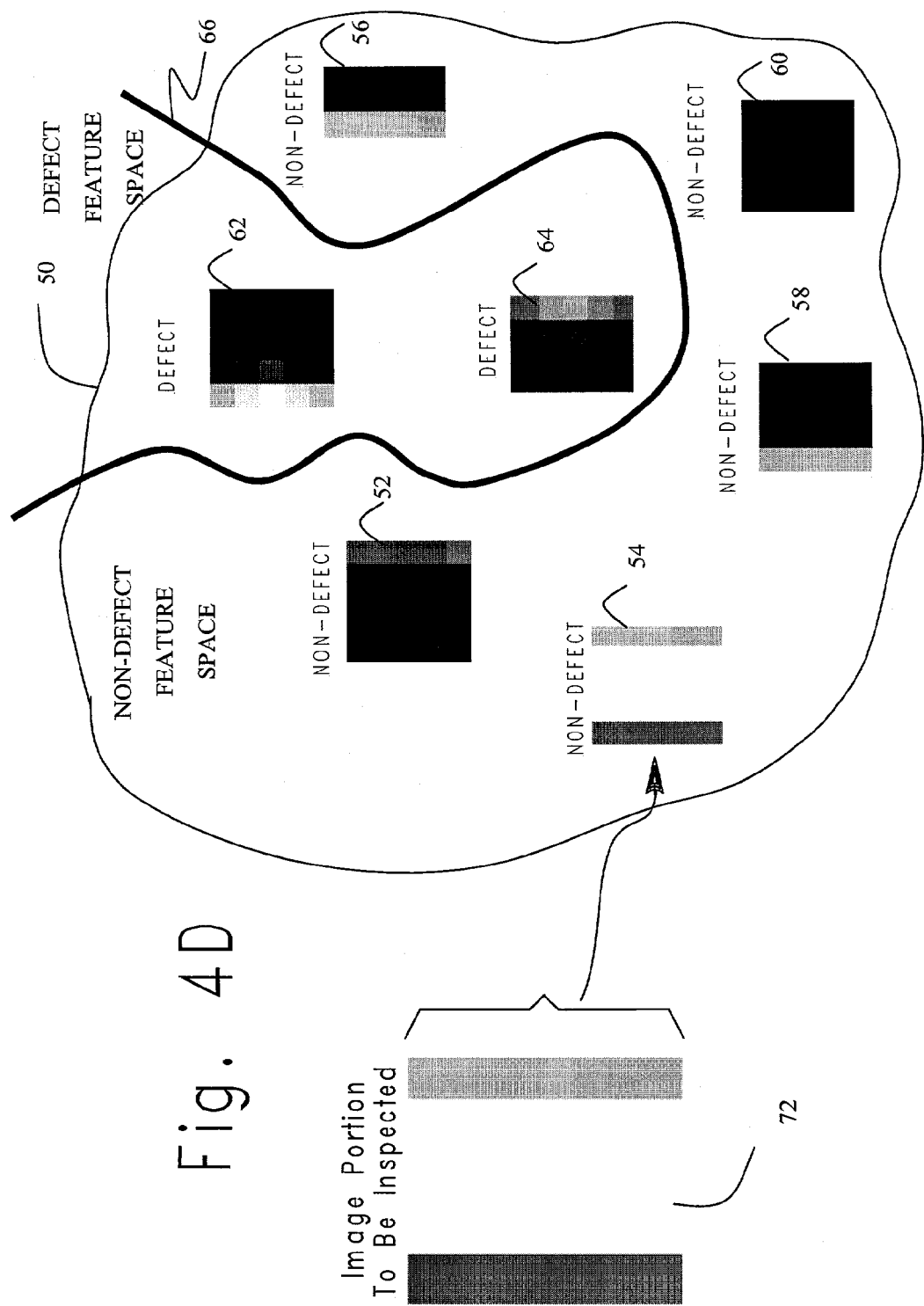

IMAGE SEARCHING DEFECT DETECTOR

CROSS REFERENCE TO RELATED APPLICATION

This application claims the benefit of U.S. Provisional Patent Application No. 60/290,010, filed May 11, 2001, the disclosure of which is incorporated by reference in its entirety.

FIELD OF THE INVENTION

The following invention relates to defect detection in the inspection of electrical circuits, and more particularly to defect detection using image classification and supervised learning systems.

BACKGROUND OF THE INVENTION

Electrical circuit inspection systems are well known, and include, for example, INSPIRE-9060™ and SK-75™ automated optical inspection systems available from Orbotech Ltd. of Yavne, Israel. These electrical circuit inspection systems employ multiple inspection channels.

After acquiring a gray level image, or a color image, of an electrical circuit to be inspected, in a first inspection channel an enhanced resolution binary image of the electrical circuit is generated from the acquired image and subsequently is analyzed to locate possible defects in the electrical circuit.

In parallel, in a second inspection channel, the gray level image is directly analyzed, typically to detect relatively small defects such as pinholes, copper splashes and fine short circuits. Analysis of the gray level image typically is performed with reference to various gray level characteristics of an image portion. The characteristics include a change in gray level values, such as a rise and/or a fall in gray level values, along various axes in the image portion. Very often the defects which are to be detected by gray level analysis are not readily visible to the naked eye, simply by human inspection of the gray level image. One reason for this difficulty is that the change in gray level values may appear insignificant to the naked eye, and the possible number of permutations of changes in gray level values, to be representative of defects or non-defects, can be relatively large.

SUMMARY OF INVENTION

The present invention seeks to provide improved systems and methods for analyzing gray level images to detect defects in objects such as printed circuit boards.

In accordance with an embodiment of the invention an image of an article to be inspected is acquired and preferably is broken down, or decomposed, into a multiplicity of image portions. Each image portion is supplied to an image search engine, or image classifier, where a search is conducted in a data base representing a plurality of labeled reference images to determine whether the image portion corresponds to a defect or non-defect. One way that this is done is to find the reference image or images to which the image portion is most similar. At least one of the reference images is labeled as corresponding to a defect and at least one of the reference images is labeled as corresponding to an absence of a defect. A report of those reference images portions found to be most similar to a reference image of a defect is provided.

In accordance with an embodiment of the invention, the reference images are represented by a plurality of representative features each of which has a defining characteristic. Such features include, for example, a trend in gray level intensity along one or more axes in the image. The characteristics of representative features are characterized in the image portions, and the characteristics of representative features of the image portions are compared to the representative features of the various reference image portions representing defects and absence of defects.

Determinations whether an image portion represents a defect or a non-defect may be made on the basis of finding the most similar labeled reference image, for example based on an analysis of the selected features associated with each of the reference images.

Optionally, representative features are determined for the image portions, and values, representing for example a relative strength of the feature, associated with an image portion to be inspected are assigned for each of the features. The values of such features may be considered defect detection values. The possible values for the collection of features form a feature space. The feature space may be, and typically is, multi-dimensional. Values associated with the features in a collection of reference images are analyzed for selected images representative of defects and non-defects, and the feature space is apportioned between portions of the space corresponding to feature compositions associated with defects and compositions of the space associated with non-defects. The values of features associated with acquired images are plotted in the feature space, and a defect determination is made as a function of whether the location of the values associated with an acquired image fall in portions of the feature space corresponding to defects or corresponding to non-defect.

The image portions comprise, for example, an array of 5×5 pixels. Typically between $10^9 - 5 \times 10^9$ image portions are independently evaluated for each image of an article to be inspected.

In accordance with an embodiment of the invention, the image search engine, or classifier, serves as an initial defect filter operative to select candidate image portions corresponding to possibly defective parts in the article being inspected, and thereby reduce data for downstream image processing. The image portions that are reported as corresponding to defects may be supplied, for example, to a further processor that applies a different, and typically more accurate, set of defect detection algorithms. Optionally, an additional image, typically having higher resolution than the image portions, is acquired of each image portion corresponding to a candidate defect, and its surroundings, and the additional image is analyzed to determine whether the candidate defect is indeed a defect or rather a false alarm.

In accordance with an embodiment of the invention, the image search engine is configured and its sensitivity calibrated, for example, such that for each approximately 100–1000 image portions initially reported as being a candidate defect, only about one image portion is still reported as a candidate defect after further processing. Additionally the image search is configured and its sensitivity calibrated so that out of about $10^6$ to $10^7$ image portions evaluated and found to be not defective, no more than one image portion actually corresponds to a defect, but is falsely reported as corresponding to non defect.

In accordance with an embodiment of the invention, the labeled reference images preferably are selected by a supervised learning process in which an operator chooses representative defective and non-defective image portions, that are labeled as being defective or not-defective. The characteristics and parameters of predetermined labeled representative features are automatically extracted offline by suitable computer means and stored in a data base. A partitioning of a feature space representing defect and non-defect image portions may be revised in response to image portions that are added to the data base.

BRIEF DESCRIPTION OF DRAWINGS

The present invention will be understood and appreciated more fully from the following detailed description, taken in conjunction with the drawings in which:

FIGS. 4A and 4B are simplified pictorial diagrams illustrating the operation of an image search engine employed in the system of FIG. 1, using image portions taken from FIG. 3, in accordance with an embodiment of the invention.

FIGS. 4C and 4D are simplified pictorial diagrams illustrating the operation of an image search engine employed in the system of FIG. 1, using image portions taken from FIG. 3, in accordance with another embodiment of the invention.

DETAILED DESCRIPTION OF PREFERRED EMBODIMENTS

Figure 1:
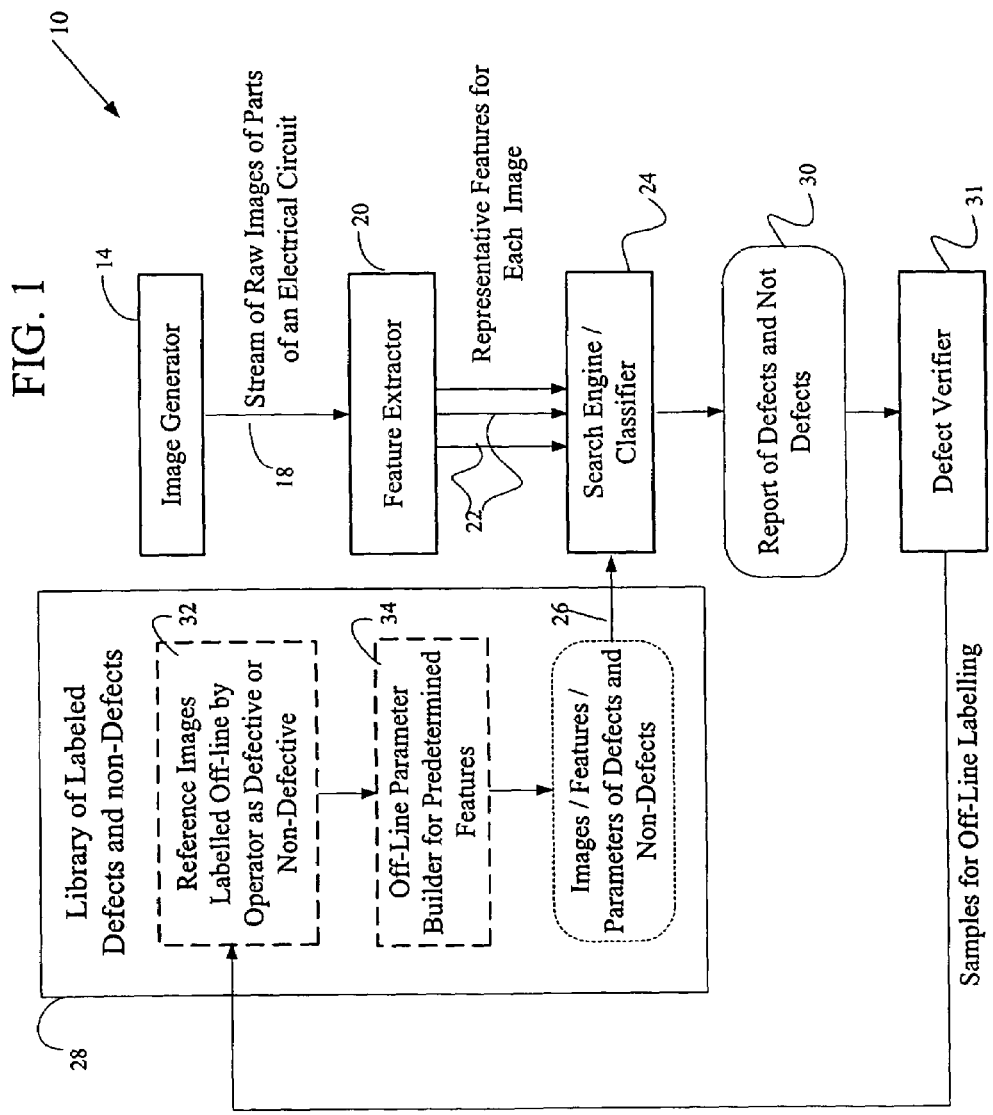
FIG. 1 is a simplified functional block diagram of a system for detecting defects in images in accordance with an embodiment of the present invention.
Figure 2:
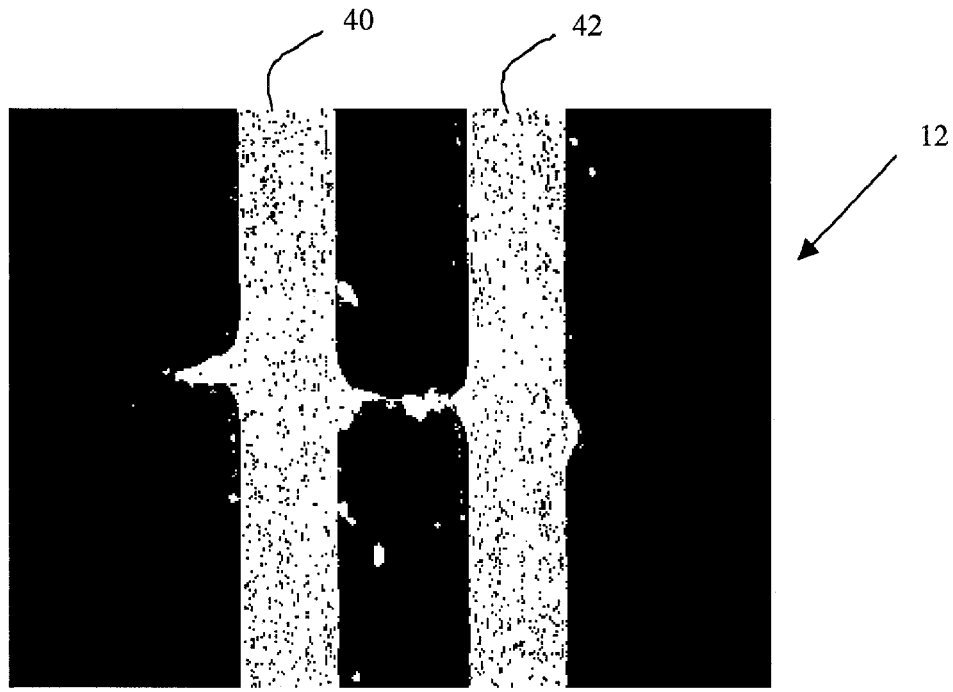
FIG. 2 is relatively high resolution black and white photograph of a portion of an electrical circuit to be inspected using the system shown in FIG. 1.
Figure 3:
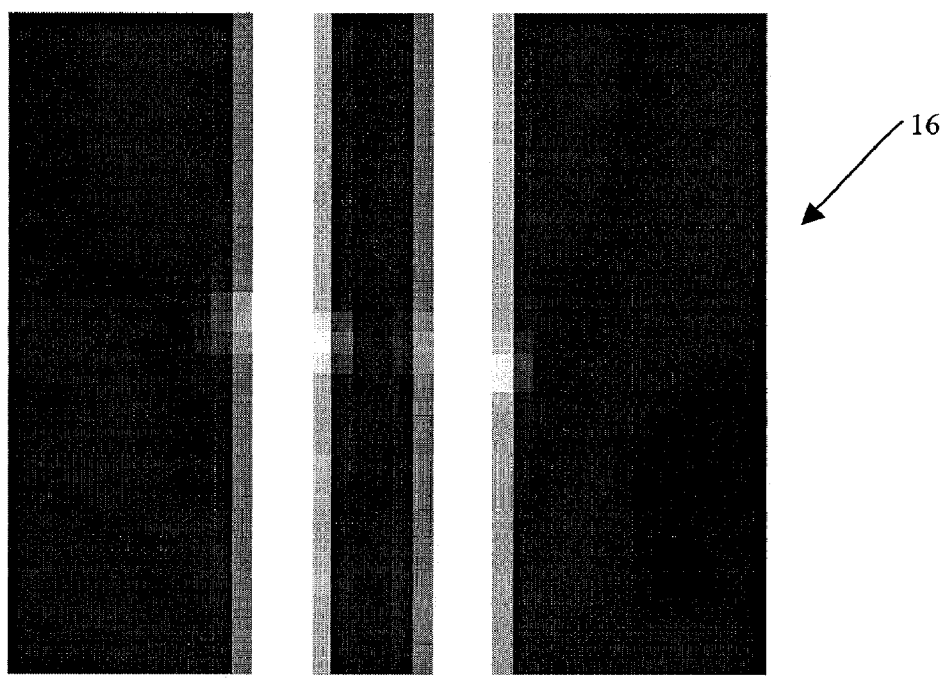
FIG. 3 is relatively low resolution digital image of the portion of the electrical circuit seen in FIG. 2, acquired in accordance with an embodiment of the invention.

Reference is made to FIG. 1, which is a simplified functional block diagram of a system 10 for detecting defects in images in accordance with an embodiment of the present invention, to FIG. 2 which is a relatively high resolution black and white photograph of an electrical circuit portion 12 to be inspected using the system of FIG. 1, and to FIG. 3 which is a relatively low resolution digital image of the portion of the electrical circuit seen in FIG. 2, acquired in accordance with an embodiment of the invention.

In accordance with an embodiment of the invention, system 10 is operative to inspect electrical circuits, including, for example, an electrical circuit portion 12 as shown in FIG. 2. Although the present invention is described in the context of inspection of electrical circuits, the system and methods described herein may be useful for inspecting images of any suitable article of manufacture, in particular electrical circuits such as printed circuit boards, ball grid array substrates, multi-chip modules and flat panel displays. Moreover, use of the term electrical circuits, as used herein, not only includes completed electrical circuits and printed circuit boards, but electrical circuit layers that may be combined together to form a completed electrical circuit.

As seen in FIG. 1, an image generator 14 generates an image 16 (FIG. 3) of an article to be inspected, for example an image of electrical circuit portion 12 (FIG. 2). Systems for acquiring digital images, such as image 16, and inspecting electrical circuits using those images (including processed representations of the electrical circuits derived from those images) are well known. Examples of such commercially available printed circuit board inspection systems include the INSPIRE-9060™ and SK-75™ systems available from Orbotech Ltd., of Yavne Israel.

In accordance with an embodiment of the invention, system 10 supplies a stream of raw image portions 18 to a feature extractor 20. Each raw image portion 18 is defined, for example, by an array of 5×5 pixels taken from an image 16, although a larger or smaller array may be used. Raw image portions 18 may be provided for selected regions of an article to be inspected, or they may be provided as a pixel neighborhood surrounding each pixel in image 18.

In accordance with an embodiment of the invention, a typical image of an electrical circuit comprises between $1\times10^9$ and $5\times10^9$ pixels. Between about $1\times10^9$ and $5\times10^9$ image portions 18, each formed of an array of 5×5 pixels, are supplied to feature extractor 20. It is desirable to configure system 10 so that it is operative to acquire and analyze all of the image portions for an electrical circuit to be inspected in an online manner, within approximately 30–60 seconds.

Feature extractor 20 preferably is provided as a dedicated hardware device operable to extract from image portions 18 one or more predetermined representative features 22 that are characteristic of an image portion and to represent these features in a predetermined format that is convenient for further processing, as is well known in the art of image searching and classification. In the context of gray level analysis of image portions employed in the inspection of electrical circuits, such image representative features may be, for example, an indication of a change in gray scale values along one or more horizontal, vertical or diagonal axes in the image portion. In accordance with an embodiment of the invention, a value is assigned to each feature, or combination of features, in an image. The value represents, for example, a relative strength of the feature in the image.

It is a feature of the present invention that representative features 22 of images 18 are supplied to a search engine 24, such as an image search engine or an image classifier, which additionally receives an input 26 from a library 28 of suitably labeled image portions of defective and non-defective parts of articles similar to the article being inspected. It is appreciated that the search engine 24 is operative to analyze features representative of an acquired image with reference to a data base of defective and not defective images, and to ascertain whether the image is representative of a defect or not a defect. In accordance with an embodiment of the invention, labeled image portions are labeled to indicate whether the image portion is indicative of a defective or non-defective portion of an electrical circuit. The labeled image portions are prepared in an offline process and are processed to extract representative features. In accordance with an embodiment of the invention, library 28 includes the representative features along with various other comparison parameters, weightings and values for those features, as would be useful for determining a degree of similarity of an image portion that is input during inspection process to one of the image portions that is stored in library 28.

It is appreciated that typically there will not be an exact match between an image portion 18 that is acquired during inspection and any particular image in library 28. Instead, in accordance with an embodiment of the invention, search engine 24 is operative to find an image portion located in library 28 to which an input image portion 18 is most similar. As previously noted, images may be stored in library 28 as a collection of representative features, a set of parameters determining similarity to a feature, and a weighting indicating a level of importance that is to be assigned to the degree of similarity found between a feature of an input image portion an corresponding feature in each of the images in the library. The use of such features, parameters and weightings is well known in the art of searching of images and defect classification.

For each image portion 18, image search engine 24 searches library 28 and identifies an image portion in library 28 to which an image portion 18 is most similar. The label associated with the image portion in library 28 indicates whether an acquired image portion 18 is defective or not defective. Preferably image search engine 24 provides a report 30 of image portions that are most similar to a library image that is labeled as a defect. Optionally, a weighting indicating a measure of similarity of an image portion 18 to a library image is provided. Such weighting can be used to calibrate the sensitivity at which system 10 operates for classifying an image portion as being representative of a candidate defect.

Alternatively, search engine 24 may be configured to generally classify acquired images 18 as corresponding to a defect or to non-defect as a function of a collection of features, without searching for the most similar labeled image in library 28. Thus in accordance with an embodiment of the invention, features that are representative of an image are determined. Reference image portions are labeled as defect and non-defect, and the respective values that associated with the reference image portions are assigned for each of the features. The values may indicate, for example, a strength of a feature in the image portion. It is appreciated that the possible values for the collection of features representing an image portion form a feature space, which may be, and typically is, multi-dimensional.

In accordance with an embodiment of the invention, the values associated with the features in reference images, which may be thought of as defect determination values, are analyzed for selected images representative of defects and non-defects, for example in off line parameter builder 34, and the feature space is apportioned between portions of the space corresponding to feature compositions associated with defects and compositions of the space associated with non-defects. Partitioning of the space may be a well defined locations. Optionally, partitioning also includes regions which are less well defined, such may be indicative of images that are questionably defective or not- defective.

The defect determination values relating to features associated with acquired images are assigned to the feature space, and a defect determination is made as a function of whether the location of the defect determination values associated with an acquired image fall in a portion of the feature space that is associated with defects or a portion of the feature space that is associated with non-defects. A weighting may also be supplied to indicate a level of confidence that a particular image portion is indeed a defect or not a defect.

It is noted that various image search engines are commercially available to receive input images and to search among a collection of images to identify an image, or images, in the collection which are most similar to the input image. It is also well known to classify images, for example as to a type of defect. These search engines and classifiers typically employ neural networks, support vector machines and/or decision tree technologies. A commercially available general purpose image search engine is the ImageHunt system available from Attrasoft of Savannah, Ga. (www.attrasoft.com). More specialized systems have also been employed in the automated optical inspection systems for inspection of integrated circuits, semiconductor wafers and liquid crystal displays to classify defects according to a type of defect, once the defects are identified upstream of the image search engine. One way to think of the search engine is as an image comparator.

In accordance with an embodiment of the invention, the search engine is configured and its sensitivity is calibrated, for example, such that for each 100–1000 image portions initially reported as being a candidate defect, only about one image portion is still reported as a candidate defect after further processing. Additionally the image search engine is configured and its sensitivity is calibrated so that out of about $10^6$–$10^7$ image portions evaluated and found to be not defective, no more than one image portion actually corresponds to a defect, but is falsely reported as corresponding to non defect. Calibration is effected, for example, by adjusting respective comparison parameters, weightings and levels of confidence that are assigned to features representing image portions in library 28.

In accordance with an embodiment of the invention, image search engine 24 is employed as a data reducer, and report 30 is supplied to a downstream defect detector, or defect verifier 31, which has a higher level of accuracy in detecting actual defects among various image portions 18 in the acquired image that is reported by search engine as being defective. The downstream defect verifier preferably applies a different set of defect detection algorithms than image search engine 24. Optionally, the downstream defect detector acquires an additional image of a location, on the electrical circuit being inspected, which has been indicated by image search engine 24 as being possibly defective. The additional image may have, for example, a higher resolution than the resolution of image portions 18. In accordance with an embodiment of the invention, the additional image is analyzed to determine whether the candidate defect, reported by image search engine 24 on the basis of analyzing an image portion 18, is indeed indicative of a defect or rather indicative of a false alarm.

Optionally, in accordance with another embodiment of the invention, defect verifier 31 is a verification station at which a human operator verifies whether a defect reported in report 30 is indeed a defect, or rather a non-defect. In such configuration of system 10, a human defect verification may be employed immediately following classification by search engine 24. Optionally, a human verification operation is performed after automated downstream defect verification such that defect verifier 31 includes at least two verification operations, at least one automatic and at least one manual.

In accordance with an embodiment of the invention, library 28, which may be thought of as a data base of image related data, is collected in an off-line mode, and, as noted above, the images included in library 28 are processed so that they may be efficiently used online during the inspection of an image. Thus, as seen in FIG. 1, library 28 includes a collection of labeled reference images 32 that are collected off line and labeled as corresponding to defective and non-defective portions of an article to be inspected. Each reference image in the collection of reference images 32 is provided to an off-line parameter builder 34 which extracts from each image in the library values relating to those features, for example corresponding to defect determination values, which are characteristic of the image portions included in the collection. Parameter builder 34 assigns one or more parameters for measuring a similarity or difference between an reference image portion and an acquired image portion, and weighting of the importance attributed to the feature.

As noted above, parameter builder may be operative to define and partition a feature space representative of the respective strengths of features in defective an non-defective image portions. The feature space may be, and typically is, multi-dimensional.

It is noted that in accordance with an embodiment of the invention, the features and values that are parameterized and stored in library 28 correspond to features that may be readily and efficiently used by image search engine 24 when searching for library images that most closely match input image portions 18. In an alternative configuration, the features correspond to those features which may be evaluated an image search engine to assign an image to be inspected to a feature space, from which defect and non-defect determinations can be made.

For example in a system for inspecting printed circuit boards for small defects such as pinholes, copper splashes, fine short circuits, and the like, such characteristic features may include one or more of gray level values for selected pixels in an image, and trends and changes in gray level values along various axes in an image portion. A conventional characterization of 5×5 image portions for small defects is employed for example in the INSPIRE-9060™ and SK-75™ AOI machines commercially available from Orbotech Ltd. of Yavne, Israel. The characterization of small defects additionally is generally discussed and described in the following U.S. patents, the disclosures of which are incorporated by reference in their entirety: U.S. Pat. Nos. 5,619,429 and 5,586,058. It is noted however that the actual composition of features and parameters used in the classification of images is not a part of the present invention, and that any suitable features may be extracted, stored and used for classification of image portions 18. Moreover, any suitable method for searching images may be employed.

Referring now to FIG. 2, there is seen a magnified photograph of a portion typical electrical circuit that may be inspected by the system shown and described with reference to FIG. 1. The circuit portion in 12 in FIG. 2 includes two conductors 40 and 42 respectively. A fine short is seen connecting between conductors 40 and 42, and a significant protrusion is seen along the left edge of conductor 40.

Referring now to FIG. 3 there is seen a digital image of the portion 12, such as is typically acquired in commercially available electrical circuit inspection systems. It is appreciated that the resolution of digital image 16 is much lower than the resolution of magnified photograph 12, and that it is difficult to readily identify the fine short or the protrusion simply by evaluation of digital image 16 with the naked eye. As seen in FIG. 3, the fine short and the protrusion are characterized by several pixels having gray level values which are different that what would be expected for pixels along a non-defective section of an edge of conductors 40 and 42, or between conductors 40 and 42. This difference can be seen by comparison of pixels in digital image 16 corresponding to neighboring portions along conductors 40 and 42.

Figure 4C:
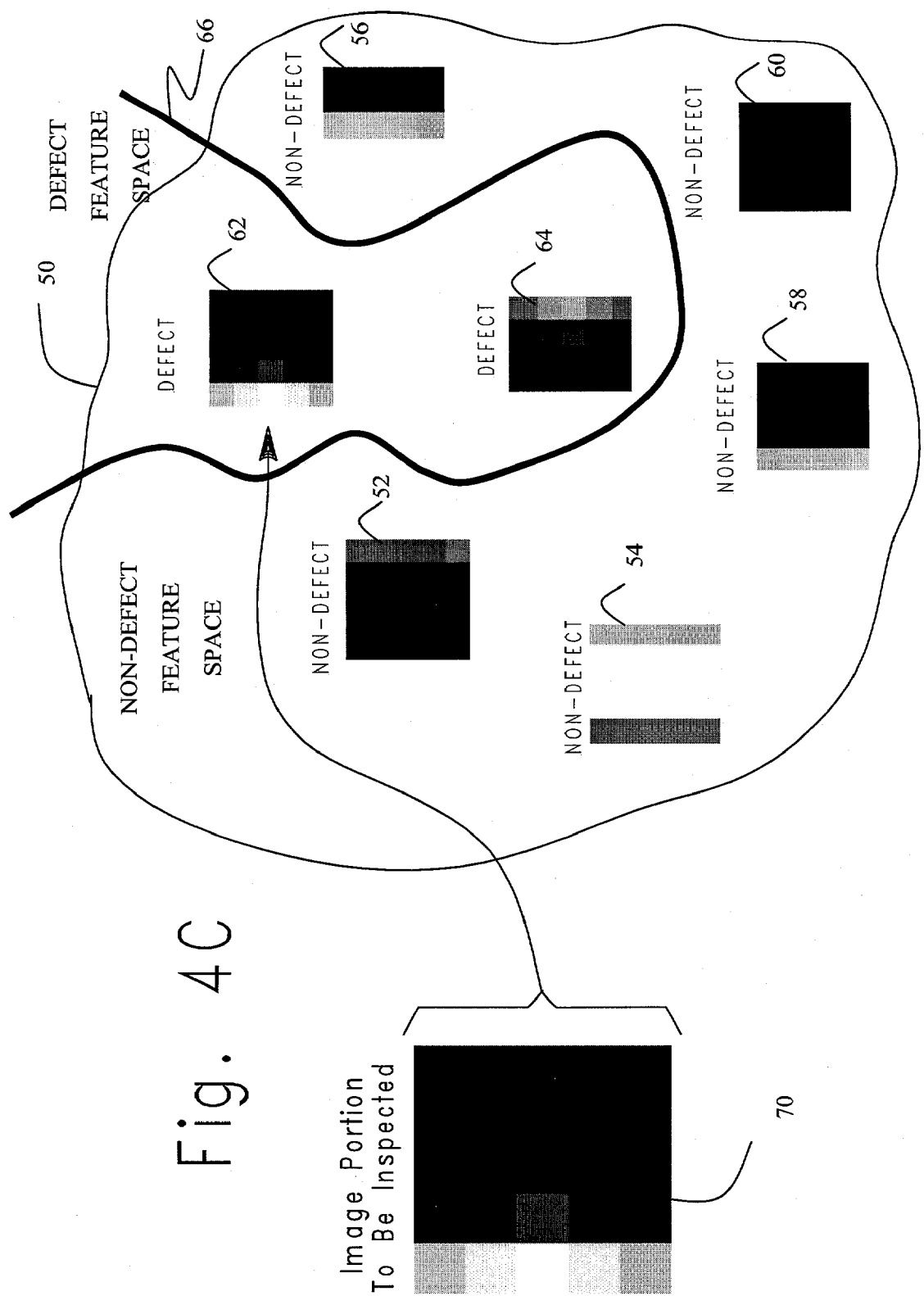

Reference is now made to FIGS. 4A and 4B, and to FIGS. 4C and 4D, which are simplified pictorial diagrams illustrating the operation of image search engine 24 employed in the system of FIG. 1. In FIGS. 4A–4D, the operation of image search engine 24 is illustrated using image portions taken from FIG. 3. In FIGS. 4A–4D a knowledge base 50 of images 52–64, such as library 28, is prepared in an offline learn mode and stored as a set of parameters as described above with reference to FIG. 1. It is appreciated that images 52–64 are shown, for the sake of simplicity, as being raw images. Moreover, for the purposes of simplicity of illustration images 52–64 are generally arbitrarily plotted in a two-dimensional image space such that knowledge base 50 can be thought of as feature space. It is noted, however, that no effort has been made in the illustrations seen in FIGS. 4A–4D to systematically organize images 52–64 according to any particular composition of features, or to show the multi-dimensional nature of the feature space.

In FIGS. 4C and 4D a partition 66 is shown separating between a portion of the feature space associated with images in knowledge base 50 that correspond to defects, and a portion of the feature space associated with images that correspond to non-defects.

Each of image portions 52–64 represents a part of the circuit seen in FIG. 2. Image portions 52–60 are portions of an acquired image 16 which correspond to non-defects in electrical circuit portion 12 (FIG. 2). Image portions 62 and 64 are portions of an acquired image 16 which correspond to defects in electrical circuit portion 12. It is noted that images 52–64 are representative of possible defects, but are not inclusive of all possible image portions and defects that may appear in an image. This is because image search engine 28 is operative to find an image portion, defective or not defective, to which an acquired image portion is a closest match, or alternatively to determine whether an acquired image portion is located in an image space associated representative of defects or representative of non-defects.

It is appreciated that image search engine thus does not require an exact match in order to determine for each acquired image portion. In fact an excess of image portions in the knowledge base may be detrimental to the efficient functioning of image search engine 24.

As seen in FIG. 4A, which corresponds to a first mode of operation, an acquired image portion 70, acquired for example by image generator 14, is compared to each of the images 52–64. An indication is made whether image portion 70 is similar or not similar to image portions 52–64, and to which image portion in knowledge base 50 image portion 70 is most similar. As seen in the example of FIG. 4A, image portion 70 is determined to be most similar to image portion 62, which is labeled as a defect. Consequently, image portion 70 would thus be reported as a defect and subjected to further processing.

As seen in FIG. 4B, which also corresponds to the first mode of operation, an acquired image portion 72, acquired for example by image generator 14, is compared to each of the images 52–64. An indication is made whether image portion 72 is similar or not similar to image portions 52–64, and to which image portion in knowledge base 50 image portion 72 is most similar. As seen in the example of FIG. 4B, image portion 72 is determined to be most similar to image portion 54, which is labeled as a non-defect. Consequently, image portion 72 would thus be reported as a non-defect, and would not be subjected to further processing.

As seen in FIGS. 4C and 4D, which corresponds to a second mode of operation, knowledge base 50 is provided as an image space in which images can be located as a function of a composition of the relative strengths of given features in an image. The image space is partitioned by partition 66 such that images of defective portions lie in an image space located on a first side of partition 66, while images of non-defective portions lie in an image space located on the other side of partition 66.

In accordance with an embodiment of the invention, each of the images is represented by a composition of strengths of various features and the location of partition 66 in the image space is analytically determined as a function those values.

As seen in FIG. 4C, image portion 70 is plotted to a location in the feature space represented by knowledge base 50. Because portion 70 is located in the portion of the image space that is associated with defects, image portion 70 is reported as corresponding to a defect.

AS seen in FIG. 4D, image portion 72 is plotted to a location in the feature space represented by knowledge base 50. Because portion 72 is located in the portion of the image space that is associated with non-defects, image portion 72 is reported as corresponding to a defect.

It is noted that the above system and method are typically employed in the manufacture of electrical circuits, such as printed circuit boards. The manufacture of electrical circuits is well known, and typically comprises forming conductive electrical circuit portions on a non-conductive substrate. Embodiments of the present invention may be employed to inspect electrical circuits during their manufacture, for example as part of quality control to ensure that the conductive electrical circuit portions are properly formed. Electrical circuits which have been inspected using the above described systems and methods, and which are found to be not defective, are subsequently incorporated into electronic devices. Electrical circuits that are found to be defective, are subsequently repaired or discarded.

It is appreciated by persons skilled in the art that the present invention is not limited by what has been particularly shown and described hereinabove. Rather the present invention includes modifications and variations thereof which would occur to a person of skill in the art upon reading the foregoing description and which are not in the prior art.

What is claimed is:

1. A method for detecting defects in electrical circuits, comprising: generating an acquired image corresponding to a part of an electrical circuit to be inspected;
   making a comparison of said acquired image with at least two reference images, at least one of said reference images representing a defect and at least one of said reference images representing an absence of a defect; and
   based on said comparison, providing an indication of a correspondence of said acquired image to a defect or to an absence of a defect.

2. The method claimed in claim 1 and wherein said acquired image is a portion of a larger image of the electrical circuit to be inspected.

3. The method claimed in claim 2 and wherein one or more representative features are extracted for each reference image, and the representative features are stored in an image library.

4. The method claimed in claim 3 and wherein a feature extracted from one of the reference images is associated with value indicating a level of strength to be attributed to such feature, and an image portion is represented by a combination of values for at least two features.

5. The method claimed in claim 4 and wherein said making a comparison comprises plotting a location of an image in a feature space as a function of said combination of values.

6. The method claimed in claim 5 and wherein said feature space includes portions that correspond to combinations of values that are indicative of defects, and portions that correspond to combinations of values that are indicative of an absence of defects.

7. The method claimed in claim 1 and wherein one or more representative features are extracted for each acquired image.

8. The method claimed in claim 1 and further comprising performing a subsequent inspection, of the electrical circuit to be inspected, at a location corresponding to an image indicated as corresponding to a defect, using an inspection method different from said making of said comparison.

9. The method claimed in claim 1 and further comprising:
   acquiring an additional image for a location corresponding to an image indicated by said comparison as corresponding to a defect; and
   inspecting said additional image using an inspection method that is different from said making of said comparison.

10. The method claimed in claim 9 and wherein said acquired image has a resolution lower than a resolution of said additional image.

11. The method claimed in claim 1 and wherein said acquired image has a resolution which is insufficiently high to enable at least some defects to be detected with an unaided eye.

12. The method claimed in claim 1 and wherein said making of said comparison is performed for at least $10^9$ images during said detecting of defects in said electrical circuit.

13. A system for inspecting electrical circuits comprising:
   an image generator generating an acquired image, said acquired image corresponding to a part of an electrical circuit to be inspected;
   an image comparator operative to compare said acquired image to at least two reference images, wherein at least one of said at least two reference images represents a defect in an image of an electrical circuit and at least one of said at least two reference image represents an absence of a defect in an image of an electrical circuit; and
   a defect indicator indicating a correspondence between said acquired image to a defect or to an absence of a defect in said electrical circuit.

14. A method for manufacturing electrical circuits, comprising:
   applying electrical conductors on a non-conductive substrate to form part of an electrical circuit, and inspecting part of an electrical circuit to be inspected, including: generating an acquired image corresponding to a part of said electrical circuit to be inspected;
   comparing said acquired image to at least two reference images, wherein at least one of said at least two reference images represents a defect in an electrical circuit and at least one of said at least two reference image represents an absence of a defect in an electrical circuit; and
   providing an indication of a correspondence of said acquired image to a defect or to an absence of a defect in said electrical circuit to be inspected.

15. A method for detecting defects in electrical circuits, comprising:
   forming a collection of images of portions of electrical circuits, said portions being classified at least as corresponding to one of a defect and a non-defect;
   for images in said collection, assigning defect determination values associated with features that represent the image, and storing said defect determination values in a memory;
   generating an acquired image corresponding to a part of an electrical circuit to be inspected;
   assigning a defect determination value for ones of said features in said acquired image;
   making an analysis of defect determination values associated with an acquired image in relation to stored defect determination values; and based on said analysis, providing an indication of a correspondence of said acquired image to a defect or to an absence of a defect.

16. The method claimed in claim 15 and wherein said forming a collection of images comprises selectively adding to said collection additional images that are classified as corresponding to a defect.

17. The method claimed in claim 16 and wherein said forming a collection of images comprises selectively adding to said collection additional images that are classified as corresponding to a non-defect.

18. The method claimed in claim 15 and wherein said forming a collection of images comprises selectively adding to said collection additional images that are classified as corresponding to a non-defect.

19. The method claimed in claim 15 and wherein said image of a portion of an electrical circuit portion of a larger image of an electrical circuit.

20. The method claimed in claim 15 and further comprising performing a subsequent inspection, of the electrical circuit to be inspected, at a location corresponding to an image indicated as corresponding to a defect, using an inspection method different from said making of said comparison.

21. The method claimed in claim 15 and further comprising: acquiring an additional image for a location corresponding to an acquired image indicated by said analysis as corresponding to a defect; and inspecting said additional image using an inspection method that is different from said making of said comparison.

22. The method claimed in claim 21 and wherein said acquired image has a resolution lower than a resolution of said additional image.

23. The method claimed in claim 15 and wherein said assigning defect determination values comprises assigning said defect determination values in a feature space.

24. The method claimed in claim 23 and further comprising apportioning said feature space to establish a portion of said feature space that is representative of defects and a portion of said feature space that is representative of non-defects.

25. The method claimed in claim 24 and wherein said making an analysis comprises determining a location of said defect determination values associated with an acquired image in said feature space.

26. The method claimed in claim 23 and further comprising: selectively adding to said collection additional images that are classified as corresponding to a defect, and adjusting said portions of feature space in response to selectively added images.

27. The method claimed in claim 15 and wherein said defect determination values represent a relative strength of a corresponding feature in an image.

* * * * *